United States Patent [19]

Fischer et al.

[11] Patent Number: 5,904,930

[45] Date of Patent: May 18, 1999

[54] TRANSDERMAL SYSTEM IN THE FORM OF A PATCH COMPRISING A TAMOXIFEN DERIVATIVE

[75] Inventors: Wilfried Fischer; Karin Klokkers; Anna Sendl-Lang, all of Holzkirchen, Germany

[73] Assignee: Hexal AG, Holzkirchen, Germany

[21] Appl. No.: 08/924,742

[22] Filed: Sep. 5, 1997

Related U.S. Application Data

[63] Continuation of application No. 08/702,668, filed as application No. PCT/EP95/00603, Feb. 20, 1995, abandoned.

[30] Foreign Application Priority Data

Mar. 8, 1994 [DE] Germany .............................. 44 07 742

[51] Int. Cl.$^6$ ...................................................... A61F 13/02
[52] U.S. Cl. ............................................ 424/448; 424/449
[58] Field of Search ...................................... 424/448, 449

[56] References Cited

U.S. PATENT DOCUMENTS

| | | | |
|---|---|---|---|
| 4,919,937 | 4/1990 | Mauvais-Jarvis | 424/449 |
| 5,132,115 | 7/1992 | Wolter | 424/449 |
| 5,474,783 | 12/1995 | Miranda | 424/448 |

*Primary Examiner*—D. Gabrielle Brouillette
*Attorney, Agent, or Firm*—Burgess, Ryan & Wayne

[57] ABSTRACT

A transdermal system in the form of a patch that comprises a tamoxifen derivative and an absorption-promoting additive for systemic administration.

14 Claims, No Drawings

TRANSDERMAL SYSTEM IN THE FORM OF A PATCH COMPRISING A TAMOXIFEN DERIVATIVE

This is a continuation of application Ser. No. 08/702,668, filed Sep. 9, 1996, now abandoned, which is a 371 of PCT/EP95/00603, filed Feb. 20, 1995.

BACKGROUND OF THE INVENTION

1. Field of the Invention

The most important medicament for the treatment of specific tumour forms, especially hormone-dependent breast tumours, is the antioestrogen tamoxifen (1-(p-3-dimethylaminoethoxyphenyl)-trans-1,2-diphenylbut-1-ene).

2. Background Art

Tamoxifen is available commercially in various oral formulations under various Trade Marks, in particular Novaldex®. Tamoxifen is administered perorally in the long-term treatment of tumours at from 10 to 40 mg per single dose. The daily dose is from 20 to 40 mg. In the case of long-term therapy, however, tamoxifen exhibits serious undesired side-effects, for example, the paradoxical stimulation of the ovaries, which presents a limiting factor in its long-term use. During passage through the liver after absorption from the gastrointestinal tract, the active metabolite 4-hydroxytamoxifen is produced from the tamoxifen and, on a molecular basis, is more active than tamoxifen by a factor of approximately 100. That value is based on the publication by Katzenellenbogen et al. (Bioactivities, oestrogen receptor interactions, and plasminogen activator-inducing activities of Tamoxifen and Hydroxytamoxifen Isomers in MCF-7 Human Breast Cancer Assays) in Cancer Research, 44 (1984) 112–119, on MCF-7 cell lines. The substance isomeric to 4-hydroxytamoxifen, 3-hydroxytamoxifen (Droloxifen), likewise binds very much more strongly to oestrogen receptors in vitro, that is by a factor of from 20 to 60, than tamoxifen itself. As in the case of 4-hydroxytamoxifen, the oestrogenically active component is less than in tamoxifen, whereas the antioestrogenic activity is in each case higher. The oestrogenic component of both tamoxifen and its hydroxy derivatives is associated with the stereoisomeric E-form, whilst the antioestrogenic component results from the Z-form. The hydroxy derivatives of tamoxifen undergo extensive metabolisation in the liver, at any rate after oral administration, as described, for example, by DE-C-2 807 599. The substances are very rapidly conjugated and thereby inactivated (Rochefort et al, (Cellular and molecular mechanism of action of antioestrogens) in J. Steroid Biochem., 19 (1983) 69–74).

On account of the high receptor affinity of hydroxytamoxifen derivatives, their therapeutic use would be desirable but, using the peroral route, it is very severely restricted because of their rapid inactivation in the liver. For that reason EP-B-0 169 214 and EP-B-0 151 326 describe the topical administration of 4-hydroxytamoxifen in an aqueous/alcoholic gel. The gel is provided for the topical application of 4-hydroxytamoxifen. In Cancer Research, 46 (1986) 1521–1525, Mauvais-Jarvis et al describe the topical administration of an alcoholic solution to 12 female patients. In that study, the distribution of radioactive 4-hydroxytamoxifen in breast tissue was examined. The authors discovered that the percutaneous topical application of 4-hydroxytamoxifen resulted first of all in a high retention of the active ingredient in the oestrogen receptor-containing breast tissue and transition to the plasma compartment was delayed for a very prolonged period. Only approximately 0.5% of the dose applied was found unchanged in the plasma.

The provision of a systemic method of administration is desirable, however, in the case of, for example, metastasising tumours, where 4-hydroxytamoxifen cannot be administered topically in every case. The percutaneous form of medicament described in the above-mentioned EP-B publications, that is the aqueous/alcoholic gel, is disadvantageous. Such gels cannot be applied per se to defined cutaneous areas, and cannot be protected from external influences, such as being washed off, or rubbed off by clothing, during the period of action. The delivery of active ingredient from such gels is accordingly very variable and unreliable.

The problem underlying the invention is to make available a systemic method of administration for tamoxifen derivatives.

SUMMARY OF THE INVENTION

The problem underlying the invention is solved by a transdermal system in the form of a patch that comprises ea tamoxifen derivative and an absorption-promoting additive. The tamoxifen derivative is thus provided in the form of an active ingredient patch, a so-called transdermal system, for systemic delivery. Since tamoxifen derivatives, such as, for example, 3-hydroxytamoxifen or 4-hydroxytamoxifen, are very lipophilic, they cannot penetrate the lipophilic barrier of the stratum corneum of the skin without additives. In order to provide adequate systemic delivery of tamoxifen derivatives, therefore, in accordance with the invention at least one absorption-promoting additive is added.

DESCRIPTION OF THE PREFERRED EMBODIMENTS

For example in accordance with the invention the desired tamoxifen derivative may be provided in the form of a solution in an alcohol, it being possible for the alcohol also to be used in the form of a water/alcohol mixture. The tamoxifen derivative in that case is thus in the form of an alcoholic or aqueous/alcoholic solution, in which the alcohol may be a low-boiling point alkanol having a chain length of from 1 to 8 carbon atoms, for example ethanol, or an aromatic alcohol, for example benzyl alcohol. In order further to increase permeation of the skin with respect to alcoholic solutions, that is by alcoholic solutions, which is desirable if transdermal systems that are as small as possible and suitable for practical use are to be made available, a content of vitamin E or a vitamin E derivative may be provided in addition. It was surprisingly discovered in accordance with the invention that permeation of the skin can be further increased by the addition of natural vitamin E (Copherol®). That result is all the more surprising since the addition of oleic acid, 1,8-cineol or phospholipids in amounts comparable to that of vitamin E leads instead to a decrease in permeation of the skin compared with pure ethanol. Oleic acid, 1,8-cineol and phospholipid are known to be very effective absorption promoters of, for example, sexual hormones.

In accordance with the invention, the tamoxifen derivative is present in the transdermal system preferably in the form of a saturated solution.

In accordance with a further embodiment of the invention, the transdermal system provided is a patch comprising a reservoir for the solution of the tamoxifen derivative (reservoir-type patch).

That patch according to the invention may comprise
(a) a solution-impermeable backing foil,
(b) a layer-like element having a cavity, (c) a microporous or semi-permeable membrane,
(d) a self-adhesive layer (adhesive layer) and
(e) optionally a removable backing film.

In that arrangement the layer-like element having a cavity may be formed by the backing foil and the membrane.

Alternatively, the patch according to the invention may comprise:
(a) a solution-impermeable backing foil,
(b) an open-pored foam, a closed-pore foam, a tissue-like layer or a fibrous web-like layer as reservoir,
(c) if the layer according to (b) is not self-adhesive, a self-adhesive layer (adhesive layer) and
(d) optionally a removable backing film.

Obviously, the self-adhesive layers must be compatible with the active ingredient solution.

In accordance with the invention, the backing foil may be formed from polyester, polypropylene or polyethylene, and the thickness of the backing foil may be in the range of from 4 to 60 $\mu$m, and especially from 5 to 50 $\mu$m.

In accordance with the invention, the microporous membrane can control to a varying degree the rate at which the active ingredient solution is released to the skin. The pore size may be so designed that the active ingredient solution is prevented from flowing out of the reservoir solely by surface tension with no release control being effected. It may alternatively, however, be provided with such small pores as to have a controlled effect on the rate of diffusion of the solution from the reservoir.

In accordance with the invention, the membrane may consist of an inert polymer, especially polypropylene, polyvinyl acetate or silicone.

By means of the mentioned self-adhesive layers, the entire therapeutic system can be stuck to the skin.

The invention is explained in detail in the following by Examples.

EXAMPLE 1

A saturated solution of 4-hydroxytamoxifen in 96% ethyl alcohol is added to the excised skin of hairless mice in a modified Franz cell. The amount of active ingredient permeating through 2.5 cm$^2$ into the acceptor medium (phosphate buffer pH=5.5) is measured continuously by HPLC. The amount that has permeated in 48 hours is approximately 400 $\mu$g.

EXAMPLE 2

A saturated solution of 4-hydroxytamoxifen in benzyl alcohol is examined in the above-described modified Franz cell. The amount of substance that has permeated in 48 hours is likewise approximately 400 $\mu$g.

EXAMPLE 3

A saturated solution of 4-hydroxytamoxifen in a mixture of oleic acid (10%) and ethanol (90%) is examined in the diffusion apparatus of Example 1. The amount of substance that has permeated in 48 hours is approximately 150 $\mu$g.

EXAMPLE 4

A saturated solution of 4-hydroxytamoxifen in a mixture of phospholipid (Phospholipon 80; 25%) and ethanol (75%) is examined. The amount of substance that has permeated in 48 hours is approximately 40 $\mu$g.

EXAMPLE 5

A saturated solution of 4-hydroxytamoxifen in a mixture of natural vitamin E (Copherol F 1300; 10%) and ethanol (90%) is examined in the diffusion cell according to Example 1. The amount of substance that has diffused in 48 hours is approximately 1200 $\mu$g.

EXAMPLE 6

A transdermal therapeutic system of the reservoir type, containing a saturated solution of 4-hydroxytamoxifen in 90% ethanol and 10% vitamin E, which has been closed at the skin side by a microporous membrane comprising 28% EVA (type MSX1154P) and a layer of a self-adhesive contact adhesive (type Cotran No. 9871) (both 3M Medica, D-Borken), exhibits in the Franz diffusion cell according to Example 1, on the skin of hairless mice, an amount of hydroxytamoxifen that has permeated in 48 hours of approximately 350 $\mu$g. In that case the microporous membrane is a control element, since the amount of substance that has permeated per unit of time is lower by a factor of approximately 2 than is the case with skin alone.

EXAMPLE 7

Several tests were carried out with an oestrogen-dependent human breast tumour of the type MAXF NCF7/10, which was allowed to grow in hairless mice. The active ingredient used was Z-4-hydroxytamoxifen. Details are given in the following Table.

Test 1: Control without Z-4-hydroxytamoxifen administration.

Tests 2 and 3 (comparisons): In these tests the active ingredient was administered subcutaneously in olive oil.

Tests 4 and 5 (invention): For these tests patches (TTS of the reservoir type) according to Example 6 were used, which comprised the active ingredient in 96% ethanol with the addition of 10% vitamin E (Copherol F1300). In Test 4 the patch was applied transdermally in the neck area of the test animals and in Test 5 it was applied topically to the tumour.

Test 6 (comparison): In this test the active ingredient was administered perorally.

The peroral administration of active ingredient is currently the standard treatment for carcinomas of the breast. A comparison of Test 6 with Tests 2 to 5, however, shows that the peroral administration is inferior to all other routes of administration; it should be noted when carrying out the comparison that the dose used in Test 6 was 100 times the dose used in Tests 3 to 5 and 10 times the dose used in Test 2.

A comparison of Tests 3 and 4 shows furthermore that the transdermal administration (Test 4) is equal to the subcutaneous administration (Test 3). Both Tests exhibit approximately 100 times stronger activity (based on dose/kg body weight) than the peroral administration of the active ingredient. Finally, a comparison of Tests 3 and 5 shows that the topical application gives approximately 10 times stronger activity than the subcutaneous administration.

TABLE 1

Anti-tumour effect of Z-4-hydroxytamoxifen on the subcutaneously growing human tumour MAXF NCF7/10 using various routes of administration

| Test | Treatment | Dose [mg/kg mouse day] | Route | n | day 7 | day 14 | day 21 | day 28 | Time to tumour volume 200% (days) | 400% (days) |
|---|---|---|---|---|---|---|---|---|---|---|
| 1 | Control | | | 10 | 185.5 | 285.0 | 533.7 | 601.5 | 8.0 | 17.2 |
| 2 | Z4OHTAM | 10 | SC | 5 | 167.8 | 237.5 | 356.5 | 394.9 | 10.2 | 28.4 |
| 3 | Z4OHTAM | 1 | SC | 5 | 182.8 | 273.5 | 390.8 | 512.1 | 8.3 | 21.5 |
| 4 | Z4OHTAM | 1 | trans | 5 | 153.6 | 256.9 | 577.3 | 557.5 | 10.1 | 17.1 |
| 5 | Z4OHTAM | 1 | top | 5 | 164.4 | 263.6 | 352.1 | 345.7 | 9.5 | 32.9 |
| 6 | TAM | 100 | po | 5 | 158.9 | 326.7 | 467.6 | 466.5 | 8.7 | 17.6 |

SC = subcutaneous
trans = transdermal in the neck region
top = topical, to the tumour
po = peroral
Z4OHTAM = Z-4-hydroxytamoxifen
TAM = tamoxifen citrate
n = number of animals

We claim:

1. A transdermal patch system comprising 3-hydroxytamoxifen and/or 4-hydroxytamoxifen wherein
   (i) the hydroxytamoxifen is in the form of a solution in an alcohol as an absorption-promoting additive,
   (ii) the transdermal system is provided with Vitamin E,
   (iii) the patch has a reservoir for the solution of the hydroxytamoxifen, and
   (iv) the patch is provided with:
      (a) a solution-impermeable backing foil,
      (b) a layer element having a cavity,
      (c) a microporous or semi-permeable membrane,
      (d) a self-adhesive layer and
      (e) optionally, a removable backing film.

2. Transdermal system according to claim 1, wherein the layer element having a cavity is formed by the backing foil and the membrane.

3. Transdermal system according to claim 1 or 2, wherein the backing foil is formed from polyester, polypropylene or polyethylene.

4. Transdermal system according to claim 3, wherein the backing foil has a thickness in the range from 4 to 60 μm.

5. Transdermal system according to claim 1, characterised in that the membrane consists of an inert polymer.

6. Transdermal system according to any one of the preceding claims, characterised in that the alcohol is a water/alcohol mixture.

7. Transdermal system according to claim 1 wherein the alcohol is a $C_1$ to $C_8$ alkanol or an aromatic alcohol as the absorption-promoting additive.

8. Transdermal system according to any one of the preceding claims, characterised in that the tamoxifen is in the form of a saturated solution.

9. Transdermal system according to claim 7 wherein the alkanol is a $C_{1-8}$ alkanol.

10. Transdermal system according to claim 7 wherein the alkanol is ethanol.

11. Transdermal system according to claim 7 wherein the aromatic alcohol is benzyl alcohol.

12. Transdermal system according to claim 1 wherein the backing foil has a thickness in the range from 5 to 50 μm.

13. Transdermal system according to claim 5 wherein the inert polymer is selected from the group consisting of polypropylene, polyvinyl acetate and silicone.

14. A method for the transdermal administration of a tamoxifen which comprises affixing to the skin of a host the patch of claim 1.

* * * * *